(12) United States Patent
Ba et al.

(10) Patent No.: US 10,578,448 B2
(45) Date of Patent: Mar. 3, 2020

(54) MONITORING AIR POLLUTION USING A MOBILE POLLUTION DETECTING DEVICE

(71) Applicant: INTERNATIONAL BUSINESS MACHINES CORPORATION, Armonk, NY (US)

(72) Inventors: Yu Tao Ba, Beijing (CN); Ling Yun Wang, Beijing (CN); Wen Jun Yin, Beijing (CN); Gang Zhou, Beijing (CN); Ke Xu Zou, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 71 days.

(21) Appl. No.: 15/444,853

(22) Filed: Feb. 28, 2017

(65) Prior Publication Data

US 2018/0245935 A1  Aug. 30, 2018

(51) Int. Cl.
*G01C 21/34*   (2006.01)
*G01N 33/00*   (2006.01)

(52) U.S. Cl.
CPC ..... *G01C 21/3461* (2013.01); *G01N 33/0031* (2013.01)

(58) Field of Classification Search
CPC ........... G01C 21/3461; G01N 33/0031; G01N 33/0075; G05D 2201/0207; G05D 1/0212
USPC .................................... 701/25, 415; 700/258
See application file for complete search history.

(56) References Cited

U.S. PATENT DOCUMENTS

| 7,302,313 | B2 | 11/2007 | Sharp et al. |
| 7,756,683 | B2 | 7/2010 | Kilgus |
| 8,751,045 | B2 * | 6/2014 | Wang ................ H01L 21/67253 700/258 |

(Continued)

FOREIGN PATENT DOCUMENTS

| CN | 103529167 | 1/2014 |
| WO | 2010070147 | 6/2010 |

OTHER PUBLICATIONS

Bales, Elizabeth et al., "Personal Pollution Monitoring: Mobile Real-Time Air-Quality in Daily Life", Computer Science and Engineering, UC San Diego, Apr. 2014, pp. 1-10.

*Primary Examiner* — Richard A Goldman
(74) *Attorney, Agent, or Firm* — F. Chau & Associates, LLC

(57) ABSTRACT

A computer-implemented method includes receiving historical pollution distribution data indicating a pollution distribution in a target area, determining a first searching path for a mobile pollution detecting device that prioritizes subareas in the target area that have not been recently searched relative to other subareas, determining a second searching path for the mobile pollution detecting device that prioritizes subareas in the target area that have a high measure of pollution relative to other subareas, determining whether an amount of the historical pollution distribution data exceeds a threshold amount, and transmitting a signal causing the mobile pollution detecting device to search the target area for pollution based on the first searching path when the amount of the historical pollution distribution data is less than the threshold amount or the second searching path when the amount of the historical pollution distribution data is greater than or equal to the threshold amount.

20 Claims, 7 Drawing Sheets

(56) References Cited

U.S. PATENT DOCUMENTS

| | | | |
|---|---|---|---|
| 8,907,803 B2 | 12/2014 | Martin | |
| 9,816,783 B1* | 11/2017 | Means | F41G 3/26 |
| 9,959,374 B2* | 5/2018 | Rosti | G06F 17/5009 |
| 2008/0045156 A1 | 2/2008 | Sakhpara | |
| 2009/0309744 A1* | 12/2009 | Fu | G01C 21/3461 |
| | | | 340/632 |
| 2010/0030417 A1* | 2/2010 | Fang | G05D 1/0274 |
| | | | 701/25 |
| 2012/0255439 A1* | 10/2012 | Seike | B03C 3/017 |
| | | | 95/79 |
| 2013/0124469 A1* | 5/2013 | Atamna | G05B 19/4183 |
| | | | 707/613 |
| 2015/0052975 A1 | 2/2015 | Martin | |
| 2016/0091474 A1* | 3/2016 | Griffon | G01N 33/0036 |
| | | | 702/24 |
| 2016/0328979 A1* | 11/2016 | Postrel | B64C 39/024 |
| 2017/0168487 A1* | 6/2017 | Mantripragada | G01N 29/02 |
| 2018/0041606 A1* | 2/2018 | Luo | G01D 21/00 |
| 2018/0245935 A1* | 8/2018 | Ba | G01C 21/3461 |
| 2018/0313649 A1* | 11/2018 | Bai | G01N 33/00 |

* cited by examiner

MONITORING AIR POLLUTION USING A MOBILE POLLUTION DETECTING DEVICE

TECHNICAL FIELD

The present invention relates generally to monitoring air pollution, and more particularly to dynamically measuring air pollution.

DISCUSSION OF RELATED ART

Air pollution has been a persistent problem in many different countries. Various approaches have been used to combat the issue. For example, an air pollution monitoring system may have fixed sites to monitor pollution in targeted areas. Having a sufficient number of fixed sites for accurate coverage may be cost prohibitive. Accordingly, there may be a trade off between high spatial error and high cost. To account for data gaps across an area as well as over time, interpolation methods may be used. However, accuracy may be lacking, particularly in places where air pollution may fluctuate rapidly or unpredictably due to, for example, high wind speed.

On the other hand, an air pollution monitoring system may instead use mobile observations, which has increased flexibility and lower cost compared to using fixed sites. Different surveillance strategies or path routing algorithms (e.g., random, ergodic) may be used to direct the mobile observations. However, without an effective surveillance strategy, the air pollution monitoring system may have either low spatial or temporal precision.

Accordingly, to avoid high costs, current pollution monitor systems may have low spatial or temporal precision due to insufficient coverage or large variance in air pollution over time and across different areas.

SUMMARY

According to an embodiment of the present invention, a computer-implemented method of monitoring air pollution is provided. The computer-implemented method includes receiving historical pollution distribution data indicating a distribution of pollution in a target area, determining a first searching path for a mobile pollution detecting device in the target area that prioritizes subareas in the target area that have not been recently searched relative to other subareas in the target area, determining a second searching path for the mobile pollution detecting device in the target area that prioritizes subareas in the target area that the historical pollution distribution data indicates have a high measure of pollution relative to other subareas in the target area, and determining whether an amount of the historical pollution distribution data exceeds a threshold amount. The computer-implemented method further includes transmitting a searching signal to the mobile pollution detecting device causing the mobile pollution detecting device to search the target area for pollution based on the first searching path in response to determining that the amount of the historical pollution distribution data is less than the threshold amount, and to search the target area for the pollution based on the second searching path in response to determining that the amount of the historical pollution distribution data is greater than or equal to the threshold amount.

According to another embodiment of the present invention, an air pollution monitoring system is provided. The air pollution monitoring system includes a mobile pollution detecting device including a pollution detecting sensor and a first transceiver, a second transceiver configured to receive historical pollution distribution data indicating a distribution of pollution in a target area, a memory storing a computer program and a processor that executes the computer program. The computer program is configured to determine a first searching path for the mobile pollution detecting device in the target area that prioritizes subareas in the target area that have not been recently searched relative to other subareas in the target area, determine a second searching path for the mobile pollution detecting device in the target area that prioritizes subareas in the target area that the historical pollution distribution data indicates have a high measure of pollution relative to other subareas in the target area, and determine whether an amount of the historical pollution distribution data exceeds a threshold amount. The second transceiver transmits a searching signal to the first transceiver causing the mobile pollution detecting device to search the target area for pollution based on the first searching path in response to the computer program determining that the amount of the historical pollution distribution data is less than the threshold amount, and to search the target area for the pollution based on the second searching path in response to the computer program determining that the amount of the historical pollution distribution data is greater than or equal to the threshold amount.

According to another embodiment of the present invention, a computer program product is provided. The computer program product includes a computer readable storage medium having program instructions embodied therewith. The program instructions executable by a processor cause the processor to receive historical pollution distribution data indicating a distribution of pollution in a target area, determine a first searching path for a mobile pollution detecting device in the target area that prioritizes subareas in the target area that have not been recently searched relative to other subareas in the target area, determine a second searching path for the mobile pollution detecting device in the target area that prioritizes subareas in the target area that the historical pollution distribution data indicates have a high measure of pollution relative to other subareas in the target area, determine whether an amount of the historical pollution distribution data exceeds a threshold amount, and transmit a searching signal to the mobile pollution detecting device causing the mobile pollution detecting device to search the target area for pollution based on the first searching path in response to determining that the amount of the historical pollution distribution data is less than the threshold amount, and to search the target area for the pollution based on the second searching path in response to determining that the amount of the historical pollution distribution data is greater than or equal to the threshold amount.

BRIEF DESCRIPTION OF THE DRAWINGS

The above and other features of the present invention will become more apparent by describing in detail exemplary embodiments thereof, with reference to the attached drawings.

DETAILED DESCRIPTION OF THE EMBODIMENTS

Figure 1:
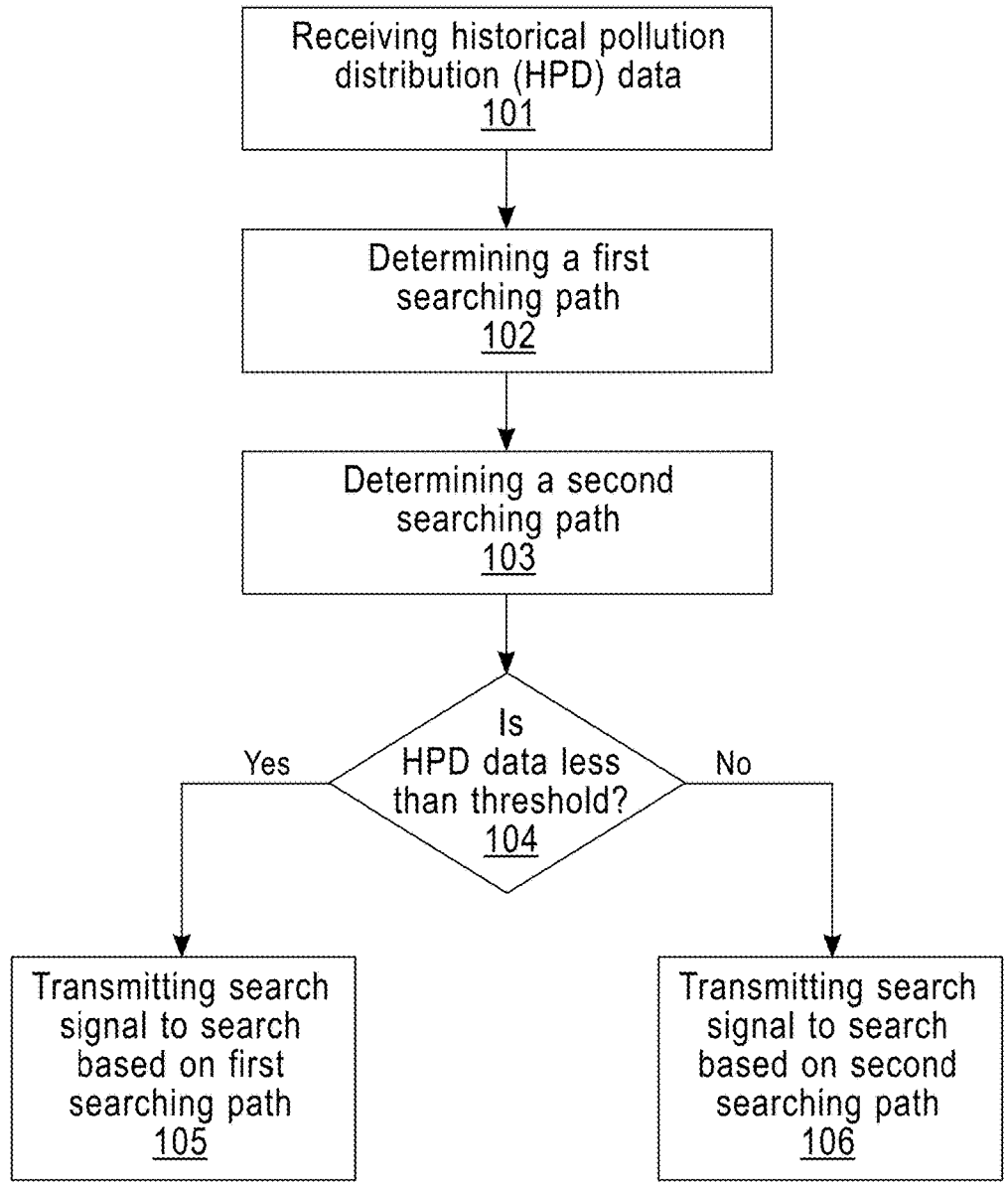
FIG. 1 is a flowchart illustrating a computer-implemented method according to an exemplary embodiment of the present invention.

Exemplary embodiments of the present invention will be described more fully hereinafter with reference to the accompanying drawings. Like reference numerals may refer to like elements throughout the specification and drawings.

Exemplary embodiments of the present invention provide a method and system of using mobile observations of air pollution to find an optimal surveillance strategy and optimal interpolation method. Accordingly, real time measurements with high spatial and temporal precision with high area coverage may be achieved using relatively low cost mobile observations.

FIG. 1 is a flowchart illustrating a computer-implemented method according to an exemplary embodiment of the present invention.

Referring to FIG. 1, historical pollution data, indicating a distribution of air pollution in a target area, is received (operation 101). The target area may be divided into a plurality of subareas to be measured or monitored.

A first searching path for a mobile pollution detecting device in the target area is determined (operation 102). The first searching path may prioritize subareas in the target area that have not been recently searched relative to other subareas in the target area. The first searching path may be referred to as a curiosity strategy. The mobile pollution detecting device will be further described below with reference to FIG. 4.

According to an exemplary embodiment of the present invention, the first searching path may further prioritize subareas in the target area that are further away (e.g., in distance) from a current location of the mobile pollution detecting device relative to other subareas in the target area. As such, undiscovered or unmeasured subareas of the target area may be searched.

A second searching path for the mobile pollution detecting device in the target area is determined (operation 103). The second searching path may prioritize subareas in the target area that the historical pollution distribution data indicates have a high measure of pollution relative to other subareas in the target area. The second searching path may be referred to as an attention strategy.

It is determined whether an amount of the historical pollution distribution data is less than a threshold amount (operation 104). According to an exemplary embodiment of the present invention, each of the subareas in the target area may have a time value (hereinafter referred to as a short memory value) corresponding to a duration from a current time to a most recent measurement. If a given subarea has never been measured for pollution or was measured a long time ago, it may be assigned a predetermined minimum short memory value (e.g., 0). If a given subarea has just been measured, it may be assigned a predetermined maximum short memory value (e.g., 100). In other words, the short memory value may vary, for example, from 0 to 100, depending on when the last measurement took place for a given subarea. The amount of the historical pollution distribution data may be the mean or median of the short memory values of all the subareas of the target area.

According to an exemplary embodiment of the present invention, the first searching path may prioritize subareas with relatively low short memory values, such as undiscovered or unmeasured subareas as well as subareas that have not been measured recently.

According to an exemplary embodiment of the present invention, each subarea may be assigned an attention value, which is a function of the short memory value and a last measurement value. The attention value may have an inverse relationship with the short memory value and a direct relationship with the last measurement value. Thus, if the short memory value is low, the attention value is high. If the last measurement value is high, the attention value is high. The second searching path may prioritize subareas with relatively high attention values. For example, the second searching path may prioritize a subarea that has not been measured recently and that has a latest measurement indicating a high amount of pollution.

Additionally, each of the short memory value, the attention value, and the last measurement value may be updated dynamically, e.g., at predetermined intervals. Accordingly, the first searching path or the second searching path may be optimally selected.

When it is determined that the amount of the historical pollution distribution data is less than the threshold amount (operation 104: YES), a searching signal is transmitted to the mobile pollution detecting device causing the mobile pollution detecting device to search the target area for pollution based on the first searching path (operation 105).

When it is determined that the amount of the historical pollution distribution data is greater than or equal to the threshold amount (operation 104: NO), the searching signal is transmitted to the mobile pollution detecting device causing the mobile pollution detecting device to search the target area for pollution based on the second searching path (operation 106).

Figure 2:
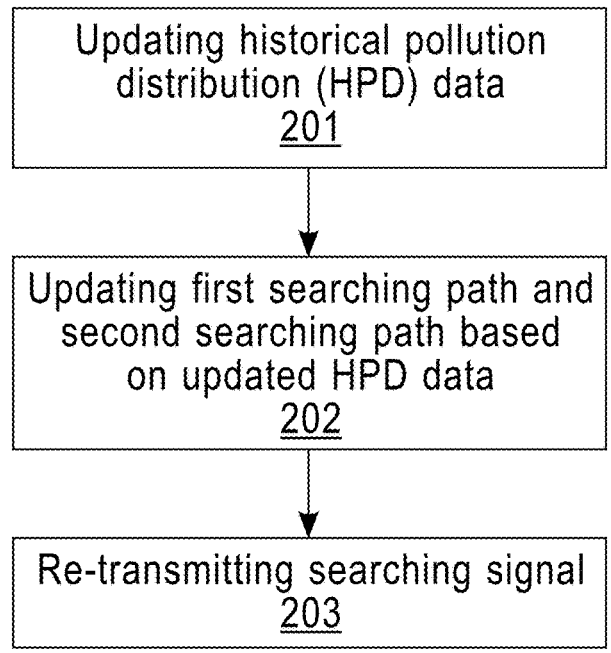
FIG. 2 is a flowchart illustrating additional operations of the computer-implemented method of FIG. 1 according to an exemplary embodiment of the present invention.

FIG. 2 is a flowchart illustrating additional operations of the computer-implemented method of FIG. 1 according to an exemplary embodiment of the present invention.

Referring to FIG. 2, the historical pollution distribution data is updated in response to the mobile pollution detecting device searching the target area for pollution (operation 201). For example, pollution measurements may be updated as well as short memory values and attention values of the subareas.

The first searching path and the second searching path are updated based on the updated historical pollution distribution data (operation 202). Accordingly, the first and second searching paths may accurately reflect the newest pollution information obtained by the mobile pollution detecting device.

The searching signal is re-transmitted to the mobile pollution detecting device in response to updating the first searching path and the second searching path (operation 203). As such, the mobile pollution detecting device may continue on an optimal path for monitoring air pollution.

Figure 3:
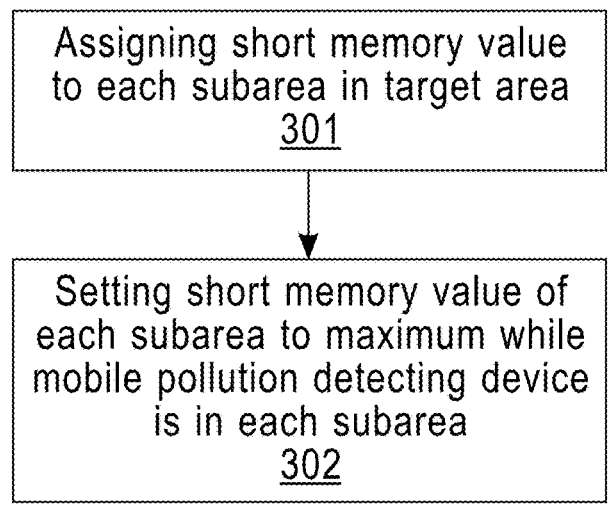
FIG. 3 is a flowchart illustrating additional operations of the computer-implemented method of FIG. 1 according to an exemplary embodiment of the present invention.

FIG. 3 is a flowchart illustrating additional operations of the computer-implemented method of FIG. 1 according to an exemplary embodiment of the present invention.

Referring to FIG. 3, a short memory value is assigned to each subarea in the target area (operation 301). For example, in a target area that has never been measured, each subarea may have its short memory value set to the predetermined minimum short memory value (e.g., 0).

The short memory value of each subarea is set to a maximum value while the mobile pollution detecting device is in each subarea (operation 302). For example, as described above, when the mobile pollution detecting device is in a given subarea, the short memory value of that subarea may be set to the predetermined maximum short memory value (e.g., 100).

The short memory value of each subarea may continuously decrease while the mobile pollution detecting device is not in each subarea. The rate at which the short memory value of each subarea continuously decreases may be modified according to an environmental factor in each subarea. For example, if wind speed is high in a subarea, the rate of decrease may be relatively high because the wind may quickly change the amount of air pollution in the subarea, necessitating more frequent measurements. Other environmental factors that may affect pollution include proximity to pollution sources, topography, precipitation, temperature, etc.

Referring to FIGS. 1 and 3 together, according to an exemplary embodiment of the present invention, determining the first searching path (operation 102 of FIG. 1) may include prioritizing subareas in the target area that have a low short memory value relative to other subareas in the target area. According to an exemplary embodiment of the present invention, determining the first searching path may include prioritizing subareas in the target area that have the minimum short memory value.

According to an exemplary embodiment of the present invention, operations described with reference to FIGS. 1 to 3 may be embodied as program instructions executable by a processor. The program instructions may be stored in a computer readable storage medium of a computer program product. This configuration will be described further below with reference to FIG. 8.

Figure 4:
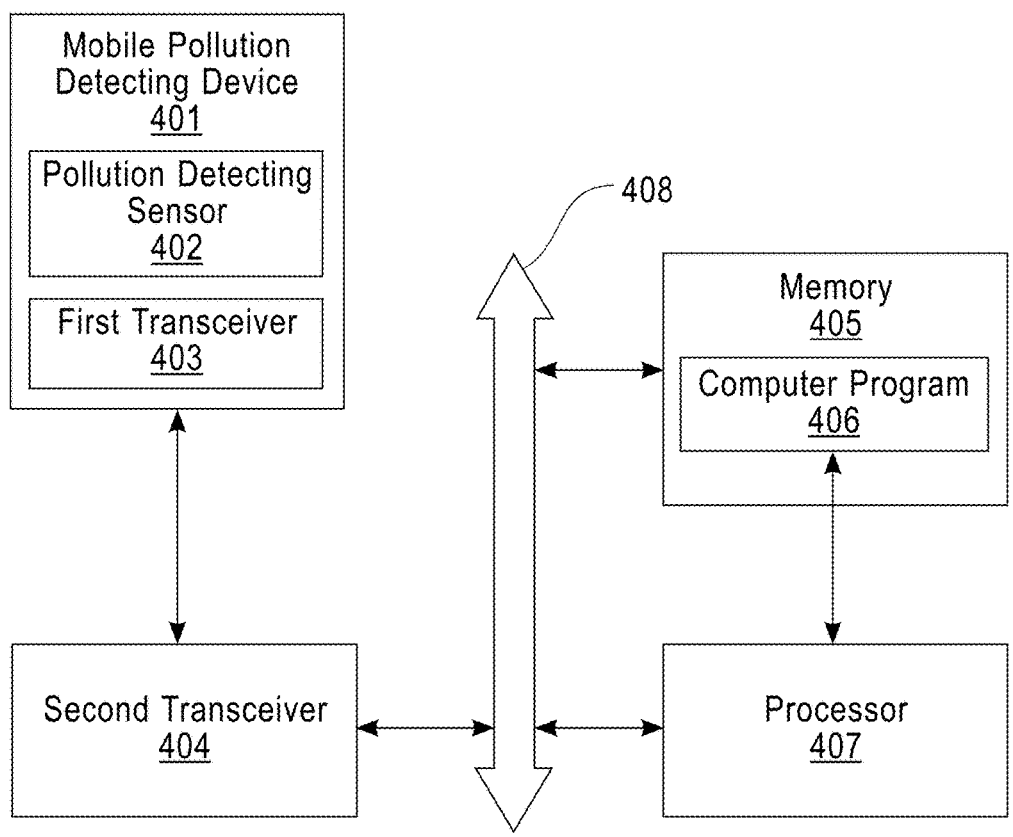
FIG. 4 illustrates a functional block diagram of a system according to an exemplary embodiment of the present invention.

FIG. 4 illustrates a system according to an exemplary embodiment of the present invention.

Referring to FIG. 4, a system 400 includes a mobile pollution detecting device 401 with a pollution detecting sensor 402 and a first transceiver 403, a second transceiver 404, a memory 405 storing a computer program 406, and a processor 407.

The mobile pollution detecting device 401 may include one or more pollution detecting sensors 402. The pollution detecting sensor 402 is a sensor that detects pollution and/or other environmental conditions. The pollution detecting sensor 402 may be, for example, an air pollution sensor that detects pollution in air, a temperature sensor, a humidity sensor, a radiation sensor, etc. It is to be understood that these types of sensors are exemplary, and that the pollution detecting sensor 402 is not limited thereto.

The second transceiver 404, the memory 405, and the processor 407 may communicate with one another via a bus 408. The first transceiver 403 and the second transceiver 404 may communicate with each other through wireless communications.

The mobile pollution detecting device 401 may be an autonomous vehicle or drone. It may also be manually operated. Alternatively, the mobile pollution detecting device 401 may be a device/sensor that can be carried or worn by a person. As another example, the mobile pollution detecting device 401 may be embodied as a mobile computing device, such as a smartphone, equipped with software and necessary pollution sensors. As the system 400 may include a plurality of mobile pollution detecting devices 401, each of them may be any one of the above-described examples. If more than one mobile pollution detecting device 401 is used, they may be instructed to take measurements in accordance with either the first searching path or the second searching path.

The second transceiver 404 may be configured to receive, from the mobile pollution detecting device 101, the historical pollution distribution data indicating the distribution of pollution in the target area (e.g., operation 101 of FIG. 1).

The processor 407 may be configured to execute the computer program 406 stored in the memory 405. For example, the computer program 406 may be configured to perform operations 102, 103, and 104 of FIG. 1.

Upon determining whether the amount of the historical pollution distribution data is less than the threshold amount (e.g., operation 104 of FIG. 1), the second transceiver may be configured to perform either operation 105 or 106 of FIG. 1

According to an exemplary embodiment of the present invention, the first transceiver 403 may transmit, to the second transceiver 404, recent pollution distribution data obtained by the pollution detecting sensor 402 while the mobile pollution detecting device 401 is searching the target area. The computer program 406 may update the historical pollution distribution data based on the recent pollution distribution data (e.g., operation 201 of FIG. 2). Additionally, the computer program 406 may update the first searching path and the second searching path based on the updated historical pollution distribution data (e.g., operation 202 of FIG. 2). The second transceiver 404 may re-transmit the searching signal to the first transceiver 403 in response to the computer program 406 updating the first searching path and the second searching path (e.g., operation 203 of FIG. 2).

According to an exemplary embodiment of the present invention, the computer program 406 may assign a short memory value to each subarea in the target area (e.g., operation 301 of FIG. 3). The computer program 406 may set the short memory value of each subarea to a maximum value while the mobile pollution detecting device is in each subarea (e.g., operation 302 of FIG. 3). The computer program 406 may continuously decrease the short memory value of each subarea while the mobile pollution detecting device is not in that subarea.

As described above, the first searching path may prioritize subareas in the target area that have a low short memory value relative to other subareas in the target area. Alternatively, the first searching path may prioritize subareas in the target area that have a minimum short memory value. Additionally, a rate at which the short memory value of each subarea continuously decreases may be modified by an environmental factor in each subarea.

Figure 5:
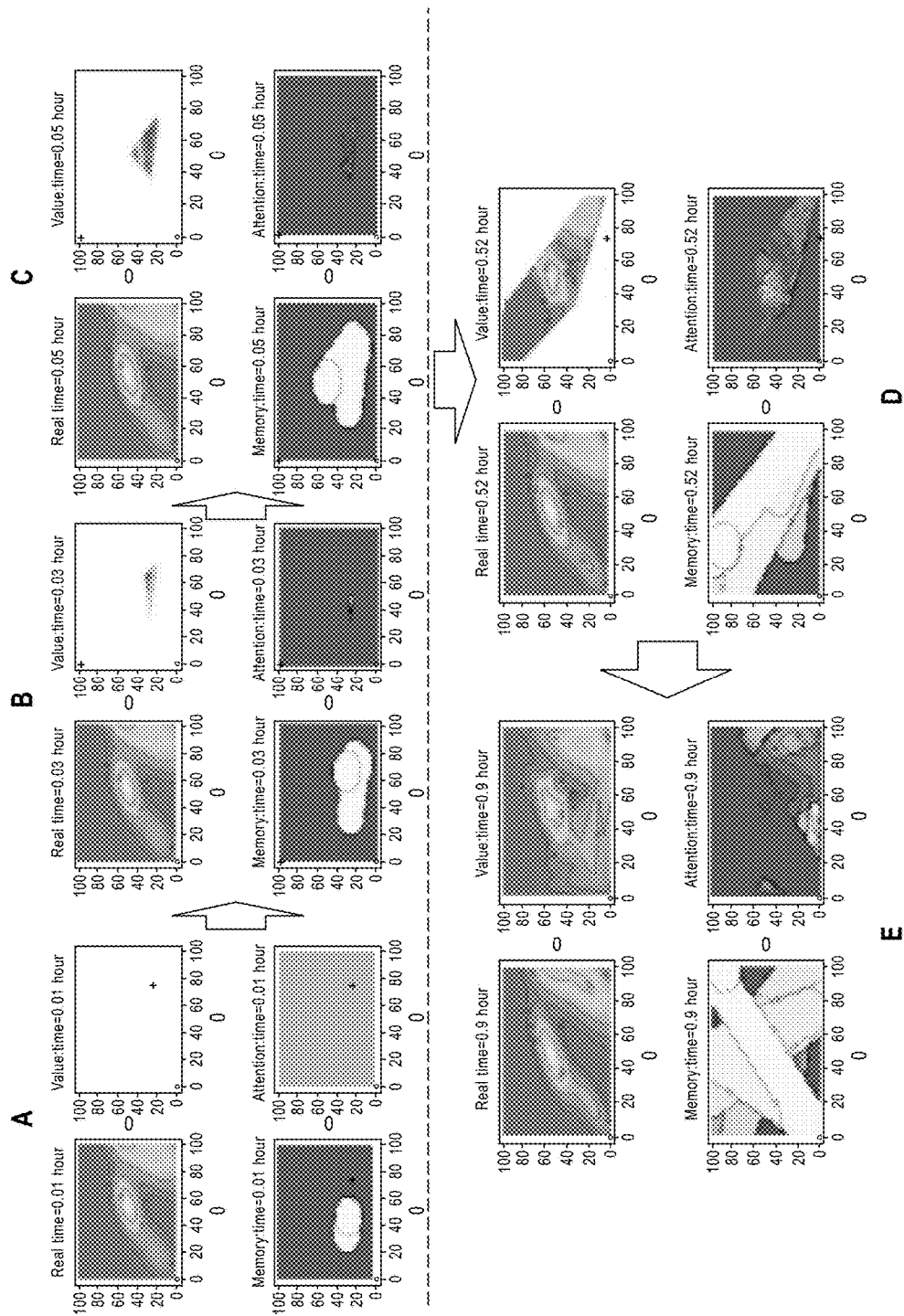
FIG. 5 is a diagram illustrating an example of performing the computer-implemented method of FIGS. 1-3 according to an exemplary embodiment of the present invention.

FIG. 5 is a diagram illustrating an example of performing the computer-implemented method of FIGS. 1-3 according to an exemplary embodiment of the present invention.

Referring to FIG. 5, phases A through E represent a progression of monitoring air pollution in the target area. Each of the phases A through E illustrates a real distribution of air pollution in the target area (top left), an estimated distribution of air pollution according to the computer-implemented method of FIGS. 1-3 (top right), a distribution of short memory values for subareas of the target area (bottom left), and a distribution of attention values for subareas of the target area (bottom right).

Referring to FIGS. 1-3 and 5, as described above, in operation 101, historical pollution data of the target area is received. In the example of FIG. 5, no historical pollution data exists for the target area as shown by the estimated distribution in phase A at 0.01 hours. As there is no historical pollution data, all subareas are undiscovered or unmeasured and have low short memory values. Accordingly, it may be determined that the historical pollution data is less than the threshold amount (operation 104) and the mobile pollution detecting device may search the target area for pollution based on the first searching path (operation 105). In this case where there is no historical pollution data, the mobile pollution detecting device may select a random direction (e.g., left or westward) to search and measure air pollution. Alternatively, the mobile pollution detecting device may move towards a target point that is furthest from its current position.

According to an exemplary embodiment of the present invention, there may be existing historical pollution distribution data before performing the operations described with reference to FIG. 1. The short memory values and attention values of the subareas may be calculated using the existing historical pollution distribution data. As such, the determination of whether to use the first searching path or the second searching path may be based on the existing historical pollution distribution data.

In transitioning between phases A through E, operations described with reference to FIG. 1 may be performed at least once between phases. Each time, operations of FIG. 2 (e.g., updating the historical pollution distribution data, the first searching path, and the second searching path) and operations of FIG. 3 (e.g., assigning and setting short memory values of the subareas) may be performed. For example, the short memory value of the subarea at which the mobile pollution detecting device is currently located may be set to the predetermined maximum short memory value, while the short memory values of all other subareas may decrease.

From phase A to phase B (at 0.03 hours), from phase B to phase C (at 0.05 hours), and from phase C to phase D (at 0.52 hours), the computer-implemented method may determine that the amount of the historical pollution distribution data is less than the threshold amount and the mobile pollution detecting device may search the target area based on the first searching path. As can be seen, over time, the estimated distribution of air pollution (top right), the short memory values (bottom left), and the attention values (bottom right) are updated, while the real distribution of air pollution (top left) is changing. The estimated distribution of air pollution may be filled out using interpolation weighted by the short memory values.

Finally, from phase D to phase E (at 0.9 hours), the computer-implemented method may determine that the amount of the historical pollution distribution data is greater than or equal to the threshold amount. Accordingly, the mobile pollution detecting device may search the target area based on the second searching path.

Figure 6:
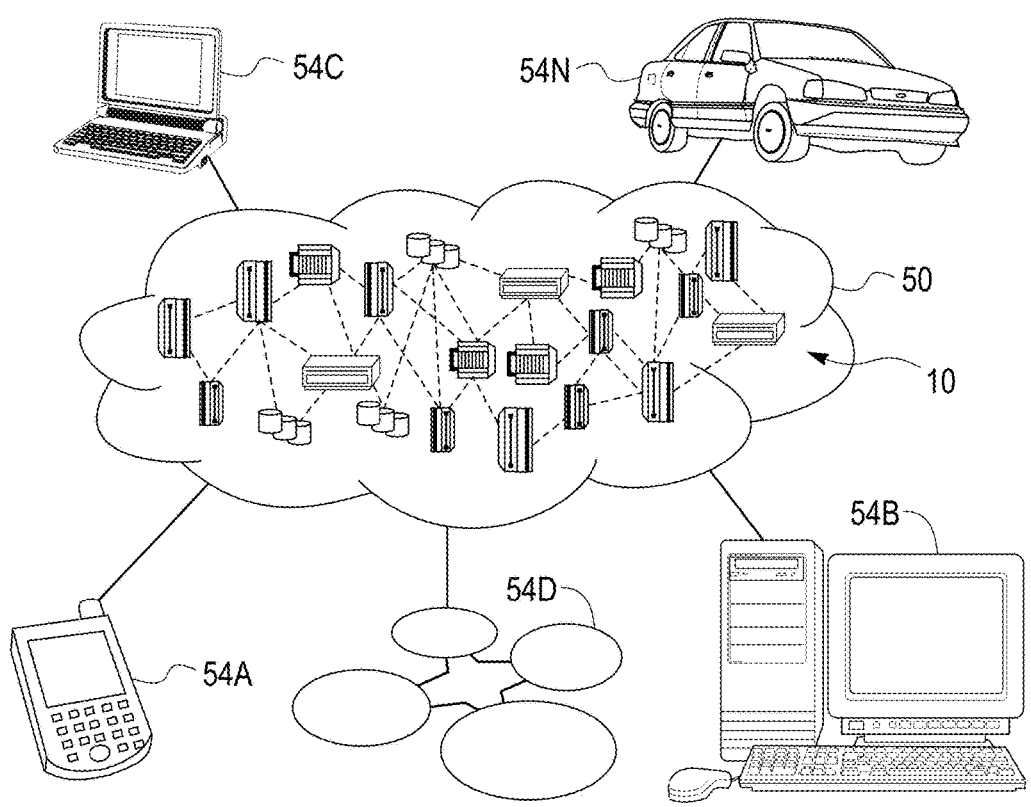
FIG. 6 depicts a cloud computing environment according to an exemplary embodiment of the present invention.
Figure 7:
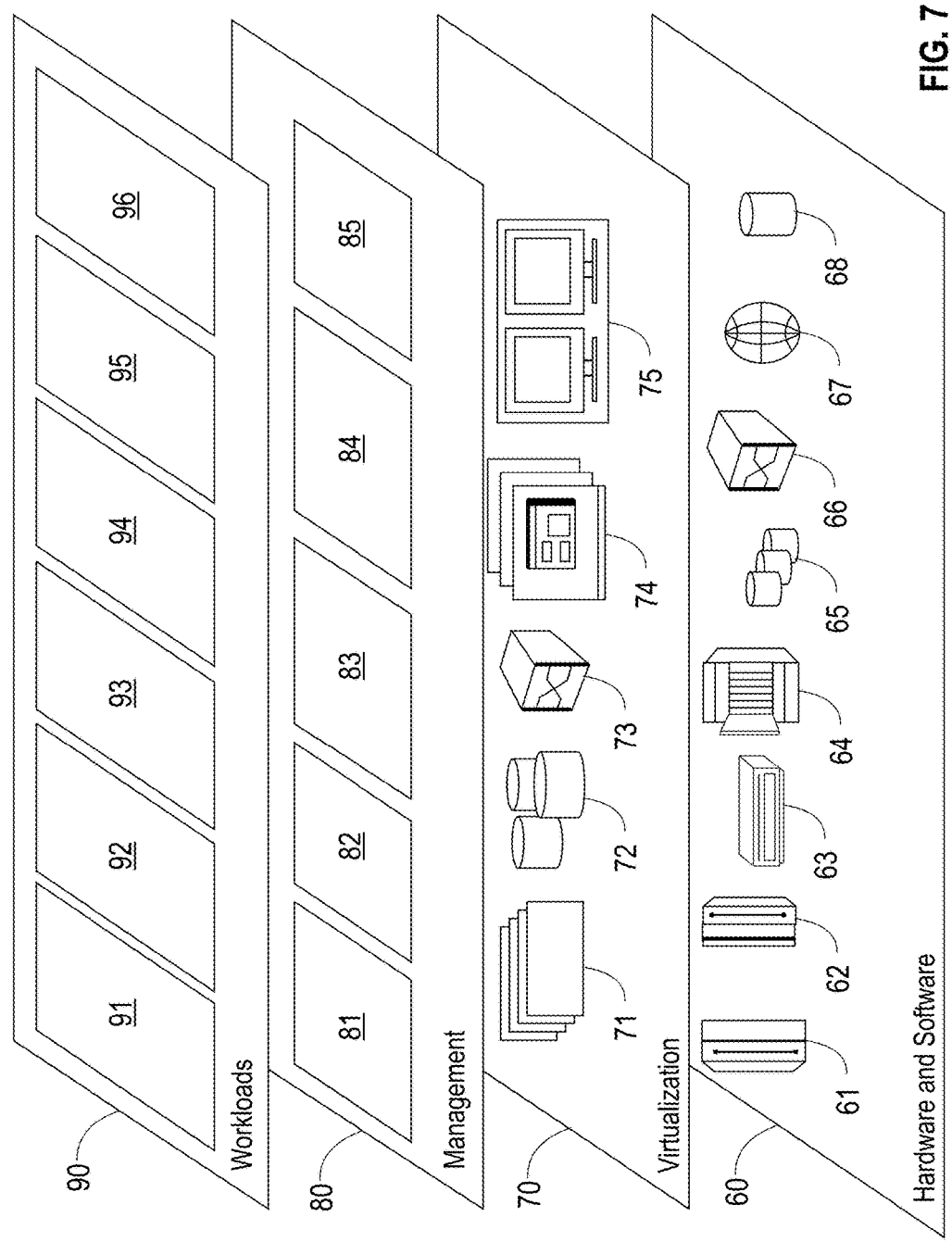
FIG. 7 depicts abstraction model layers according to an exemplary embodiment of the present invention.

FIG. 6 depicts a cloud computing environment according to an exemplary embodiment of the present invention. FIG. 7 depicts abstraction model layers according to an exemplary embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 6, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, a drone 54D, and/or automobile computer system 54N may communicate. Nodes 10 may communicate with one another. The drone 54D may correspond to the mobile pollution detecting device 401 of FIG. 4. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a mobile pollution detecting device 96 (e.g., corresponding to the mobile pollution detecting device 401 of FIG. 4).

With respect to the system and method described above with reference to FIGS. 1 to 4, they may be configured across the plurality of layers of FIG. 7 within the cloud computing environment 50 of FIG. 6. For example, the mobile pollution detecting device 401 of FIG. 4 may be configured at the workloads layer 90, as described above. The memory 405, the processor 407, and the second transceiver 404 of FIG. 4 may be configured at the hardware and software layer 60. Alternatively, a computer program product containing program instructions to perform operations described with reference to FIGS. 1 to 3 may be configured at the hardware and software layer 60, the virtualization layer 70, the management layer 80, or the workloads layer 90.

Figure 8:
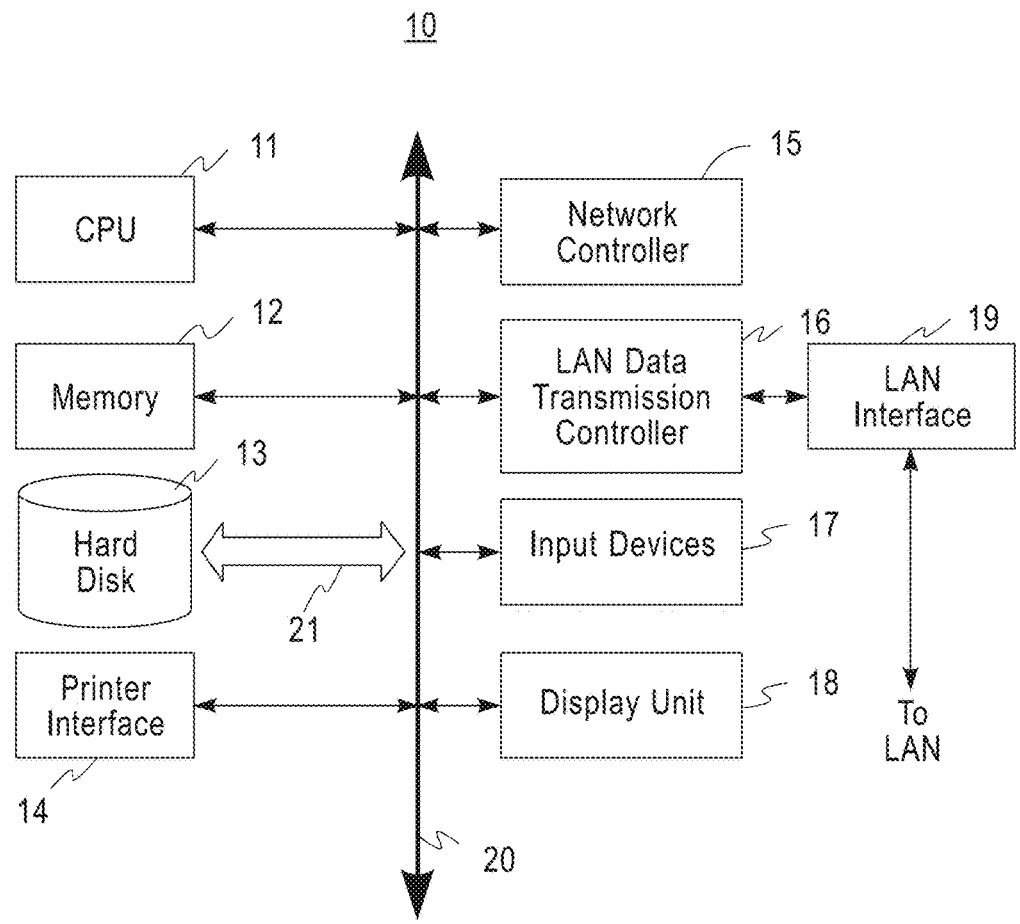
FIG. 8 illustrates an example of a computer system capable of implementing the methods according to exemplary embodiments of the present invention.

FIG. 8 illustrates an example of a computer system capable of implementing the methods according to exemplary embodiments of the present invention. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 10 may include, for example, a central processing unit (CPU) 11, random access memory (RAM) 12, a printer interface 14, a network controller 15, a local area network (LAN) data transmission controller 16, a display unit 18, a LAN interface 19, an internal bus 20, and one or more input devices 17, for example, a keyboard, mouse etc. As shown, the system 10 may be connected to a data storage device, for example, a hard disk, 13 via a link 21.

As an example, the system 10 of FIG. 8 may be correspond to the system 400 of FIG. 4 and/or be configured to perform the operations described with reference to FIGS. 1 to 3.

Moreover, the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. See, e.g., FIGS. 1-3.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As described above, according to exemplary embodiments of the present invention, the system and method for monitoring air pollution may use the first or second searching path to measure air pollution at subareas of the target area. The first searching path or the second searching path may be optimally selected based on a plurality of factors, such as the short memory value, the attention value, the last measurement value, environmental factors, etc. As such, the mobile pollution detecting device may efficiently measure and monitor different subareas, e.g., undiscovered subareas, subareas with high historical pollution, subareas with a high pollution change rate. By optimizing the searching path, fewer pollution monitors may be required, resulting in lower cost. Furthermore, higher temporal and spatial precision may be achieved.

While the present invention has been shown and described with reference to exemplary embodiments thereof, it will be understood by those of ordinary skill in the art that various changes in form and detail may be made therein without departing from the spirit and scope of the present invention as defined by the following claims.

We claim:

1. A computer-implemented method of monitoring air pollution, comprising:
   receiving, by a second transceiver, historical pollution distribution data indicating a distribution of pollution in a target area;
   determining, by a processor, a first searching path for a mobile pollution detecting device in the target area that prioritizes subareas in the target area that have not been recently searched relative to other subareas in the target area,
   wherein the mobile pollution detecting device comprises a first transceiver;
   determining, by the processor a second searching path for the mobile pollution detecting device in the target area that prioritizes subareas in the target area that the historical pollution distribution data indicates have a high measure of pollution relative to other subareas in the target area;
   determining, by the processor, whether an amount of the historical pollution distribution data is less than a threshold amount; and
   transmitting, from the second transceiver to the first transceiver, a searching signal to the mobile pollution detecting device causing the mobile pollution detecting device to search the target area for pollution based on the first searching path in response to determining that the amount of the historical pollution distribution data is less than the threshold amount, and to search the target area for the pollution based on the second searching path in response to determining that the amount of the historical pollution distribution data is greater than or equal to the threshold amount.

2. The computer-implemented method of claim 1, wherein the first searching path further prioritizes subareas in the target area that are further in distance from a current location of the mobile pollution detecting device relative to other subareas in the target area.

3. The computer-implemented method of claim 1, further comprising:
   updating the historical pollution distribution data in response to the mobile pollution detecting device searching the target area for the pollution;
   updating the first searching path and the second searching path based on the updated historical pollution distribution data; and
   re-transmitting the searching signal to the mobile pollution detecting device in response to updating the first searching path and the second searching path.

4. The computer-implemented method of claim 3, further comprising:
   assigning a time value to each subarea in the target area, wherein the time value corresponds to a duration from a current time to a most recent measurement taken in the corresponding subarea; and
   setting the time value of the each subarea to a maximum value while the mobile pollution detecting device is in the each subarea,
   wherein the time value of the each subarea decreases without increasing while the mobile pollution detecting device is not in the each subarea.

5. The computer-implemented method of claim 4, wherein said determining the first searching path prioritizes subareas in the target area that have a low time value relative to other subareas in the target area.

6. The computer-implemented method of claim 4, wherein said determining the first searching path prioritizes subareas in the target area that have a minimum time value.

7. The computer-implemented method of claim 4, wherein a rate at which the time value of the each subarea decreases is modified by an environmental factor in the each subarea.

8. An air pollution monitoring system, comprising:
   a mobile pollution detecting device comprising a pollution detecting sensor and a first transceiver;
   a second transceiver configured to receive historical pollution distribution data indicating a distribution of pollution in a target area;
   a memory storing a computer program; and
   a processor that executes the computer program, wherein the computer program is configured to:
      determine a first searching path for the mobile pollution detecting device in the target area that prioritizes subareas in the target area that have not been recently searched relative to other subareas in the target area;
      determine a second searching path for the mobile pollution detecting device in the target area that prioritizes subareas in the target area that the historical pollution distribution data indicates have a high measure of pollution relative to other subareas in the target area; and
      determine whether an amount of the historical pollution distribution data is less than a threshold amount,
   wherein the second transceiver transmits a searching signal to the first transceiver causing the mobile pollution detecting device to search the target area for pollution based on the first searching path in response to the computer program determining that the amount of the historical pollution distribution data is less than the threshold amount, and to search the target area for the pollution based on the second searching path in response to the computer program determining that the amount of the historical pollution distribution data is greater than or equal to the threshold amount.

9. The air pollution monitoring system of claim 8, wherein the mobile pollution detection device is an autonomous vehicle.

10. The air pollution monitoring system of claim 8, wherein the first searching path further prioritizes subareas in the target area that are further in distance from a current location of the mobile pollution detecting device relative to other subareas in the target area.

11. The air pollution monitoring system of claim 8,
wherein the first transceiver transmits recent pollution distribution data, obtained by the pollution detecting sensor while the mobile pollution detecting device is searching the target area, to the second transceiver,
wherein the computer program updates the historical pollution distribution data based on the recent pollution distribution data, and updates the first searching path and the second searching path based on the updated historical pollution distribution data, and
wherein the second transceiver re-transmits the searching signal to the first transceiver in response to the computer program updating the first searching path and the second searching path.

12. The air pollution monitoring system of claim 11, wherein the computer program:
assigns a time value to each subarea in the target area, wherein the time value corresponds to a duration from a current time to a most recent measurement taken in the corresponding subarea;
sets the time value of the each subarea to a maximum value while the mobile pollution detecting device is in the each subarea; and
decreases, without increasing, the time value of the each subarea while the mobile pollution detecting device is not in the each subarea.

13. The air pollution monitoring system of claim 12, wherein the first searching path prioritizes subareas in the target area that have a low time value relative to other subareas in the target area.

14. The air pollution monitoring system of claim 12, wherein the first searching path prioritizes subareas in the target area that have a minimum time value.

15. The air pollution monitoring system of claim 12, wherein a rate at which the time value of the each subarea decreases is modified by an environmental factor in the each subarea.

16. A computer program product comprising a non-transitory computer readable storage medium having program instructions embodied therewith, the program instructions executable by a processor to cause the processor to:
receive historical pollution distribution data indicating a distribution of pollution in a target area;
determine a first searching path for a mobile pollution detecting device in the target area that prioritizes subareas in the target area that have not been recently searched relative to other subareas in the target area;
determine a second searching path for the mobile pollution detecting device in the target area that prioritizes subareas in the target area that the historical pollution distribution data indicates have a high measure of pollution relative to other subareas in the target area;
determine whether an amount of the historical pollution distribution data is less than a threshold amount; and
transmit a searching signal to the mobile pollution detecting device causing the mobile pollution detecting device to search the target area for pollution based on the first searching path in response to determining that the amount of the historical pollution distribution data is less than the threshold amount, and to search the target area for the pollution based on the second searching path in response to determining that the amount of the historical pollution distribution data is greater than or equal to the threshold amount.

17. The computer program product of claim 16, wherein the first searching path further prioritizes subareas in the target area that are further in distance from a current location of the mobile pollution detecting device relative to other subareas in the target area.

18. The computer program product of claim 16, wherein the program instructions executable by the processor further cause the processor to:
update the historical pollution distribution data in response to the mobile pollution detecting device searching the target area for the pollution;
update the first searching path and the second searching path based on the updated historical pollution distribution data; and
re-transmit the searching signal to the mobile pollution detecting device in response to updating the first searching path and the second searching path.

19. The computer program product of claim 18, wherein the program instructions executable by the processor further cause the processor to
assign a time value to each subarea in the target area, wherein the time value corresponds to a duration from a current time to a most recent measurement taken in the corresponding subarea; and
set the time value of the each subarea to a maximum value while the mobile pollution detecting device is in the each subarea,
wherein the time value of the each subarea decreases while the mobile pollution detecting device is not in the each subarea.

20. The computer program product of claim 19, wherein the first searching path prioritizes subareas in the target area that have a low time value relative to other subareas in the target area.

* * * * *